(12) United States Patent
Kissell et al.

(10) Patent No.: US 11,814,337 B2
(45) Date of Patent: Nov. 14, 2023

(54) PROCESS FOR RECOVERING ACETONITRILE

(71) Applicant: Ascend Performance Materials Operations LLC, Houston, TX (US)

(72) Inventors: Kyle Kissell, Houston, TX (US); Basil Michaels, Houston, TX (US)

(73) Assignee: Ascend Performance Materials Operations LLC, Houston, TX (US)

( * ) Notice: Subject to any disclaimer, the term of this patent is extended or adjusted under 35 U.S.C. 154(b) by 29 days.

(21) Appl. No.: 17/466,882

(22) Filed: Sep. 3, 2021

(65) Prior Publication Data

US 2022/0064108 A1     Mar. 3, 2022

Related U.S. Application Data

(60) Provisional application No. 63/074,316, filed on Sep. 3, 2020.

(51) Int. Cl.
    *C07C 253/34*      (2006.01)
    *B01D 3/14*      (2006.01)

(52) U.S. Cl.
    CPC ............ *C07C 253/34* (2013.01); *B01D 3/143* (2013.01)

(58) Field of Classification Search
    CPC .............................. C07C 253/34; B01D 3/143
    See application file for complete search history.

(56) References Cited

U.S. PATENT DOCUMENTS

| | | |
|---|---|---|
| 4,308,108 A | 12/1981 | Higuchi et al. |
| 4,362,603 A | 12/1982 | Presson et al. |
| 6,780,289 B2 | 8/2004 | Godbole |
| 2020/0157044 A1 | 5/2020 | Michael et al. |

FOREIGN PATENT DOCUMENTS

| | | |
|---|---|---|
| EP | 0937707 B1 | 4/2003 |
| WO | 02/06212 A2 | 1/2002 |

*Primary Examiner* — Sikarl A Witherspoon
(74) *Attorney, Agent, or Firm* — COZEN O'CONNOR

(57) ABSTRACT

A process for producing acetonitrile, the process comprising: treating a feedstock stream comprising methanol, allyl alcohol, oxazole, acetonitrile, water, and hydrogen cyanide to remove hydrogen cyanide and produce an acetonitrile stream comprising less than 1 wt. % hydrogen cyanide. The process further comprises the step of distilling the acetonitrile stream in a first distillation column to produce a first distillate comprising oxazole and methanol; a first intermediate acetonitrile stream comprising acetonitrile and oxazole and less than 1 wt % allyl alcohol; a first bottoms stream comprising allyl alcohol and water. The process further comprises the step of purifying the first intermediate acetonitrile stream to produce an acetonitrile product stream and a recycle stream comprising allyl alcohol.

20 Claims, 1 Drawing Sheet

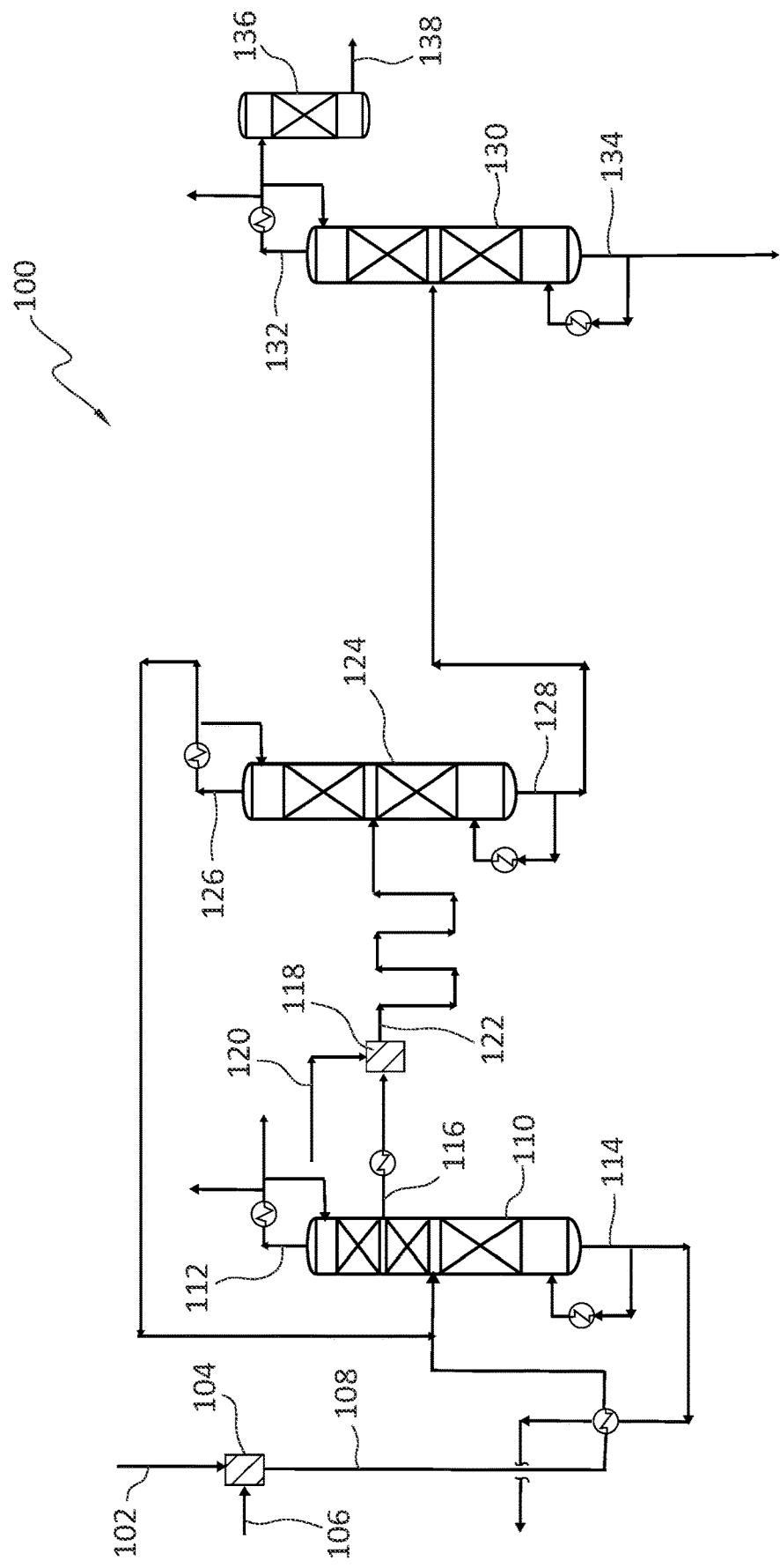

PROCESS FOR RECOVERING ACETONITRILE

CROSS REFERENCE TO RELATED APPLICATIONS

This application claims priority to U.S. Provisional Application No. 63/074,316, filed Sep. 3, 2020, which is incorporated herein by reference.

FIELD

The present disclosure relates generally to recovery of acetonitrile from industrial processes. More specifically, the present disclosure relates to process for recovering acetonitrile from acrylonitrile waste streams comprising allyl alcohol, oxazole, and methanol.

BACKGROUND

Cyanocarbons, e.g., organic compounds having cyano functional groups, are known and are widely used in various applications. Many of these compounds, including acrylonitrile, are used as monomers to prepare various polymers, such as nylon, polyacrylonitrile, or acrylonitrile butadiene styrene. Several methods of producing cyanocarbons are known in the art, and these production methods often yield waste streams comprising small amounts of desirable coproducts. For example, acetonitrile may be present in many of the conventional waste streams of industrial acrylonitrile production processes. Typically, this co-product acetonitrile is recovered using well-known separation schemes. These acrylonitrile process waste stream separation schemes, however, have been found to be suffer from efficiency problems, especially when lower acetonitrile concentrations are present. Importantly, many conventional separation schemes do not contemplate the presence of some impurities in the waste streams, e.g., allyl alcohol, oxazole, and methanol, which have been found to be particularly precarious to isolate. As one example, methanol separation is difficult because of its propensity to azeotrope with acetonitrile.

A number of processes for recovering acetonitrile are known in the art. For example, U.S. Pat. No. 4,362,603 discloses a process for recovering an acetonitrile byproduct from a stream comprising acetonitrile, water, HCN, acrylonitrile, and other organics such as oxazole, allyl alcohol, acetone, or propionitrile by distilling in three distillation zones at varying pressures.

As another example, U.S. Pat. No. 6,780,289 discloses a method for the purification of crude acetonitrile comprising distilling the crude acetonitrile in a first fractional distillation column at below atmospheric pressure, withdrawing a first side draw fraction comprising acetonitrile, distilling the first side draw fraction in a second fractional distillation column at super atmospheric pressure, and withdrawing from the second distillation a second side draw fraction comprising purified acetonitrile.

While these references may relate to acetonitrile separation, these references fail to contemplate unique feedstock streams that comprise allyl alcohol, oxazole, and methanol, inter alia. Thus, the need exists for improved processes that effectively separate and/or recover high purity by-product acetonitrile from acrylonitrile production process waste streams.

SUMMARY

In some embodiments, the present disclosure relates to a process for producing acetonitrile, the process comprising the step of treating a feedstock stream to remove hydrogen cyanide and produce an acetonitrile stream comprising less than 1 wt. % hydrogen cyanide. The feedstock stream may comprise (greater than 0.05 wt. %) methanol, allyl alcohol, oxazole, (less than 25 wt. %) acetonitrile, water, and hydrogen cyanide, and optionally oxazole and/or propionitrile. The process may further comprise the step of distilling the acetonitrile stream (in a first distillation column, optionally operating at a pressure ranging from 100 kPa to 175 kPa) to produce: a first distillate, a first intermediate acetonitrile stream, and a first bottoms stream. The first distillate may comprise (greater than 1 wt %) oxazole and (greater than 5 wt %) methanol. The first intermediate acetonitrile stream may comprise (greater than 25 wt %) acetonitrile, (less than 5 wt %) oxazole, (less than 50 wt %) water, and less than 1 wt %, allyl alcohol, (less than 0.05 wt % or less than 0.01 wt %) hydrogen cyanide, and may be a sidedraw, optionally taken in the upper 70% of the column. The first bottoms stream may comprise (greater than 0.01 wt %) allyl alcohol and (greater than 75 wt %) water. The process may further comprise the step of purifying the first intermediate acetonitrile stream to produce an acetonitrile product stream and a recycle stream comprising allyl alcohol. The recycle stream may comprise a smaller amount of allyl alcohol than the first bottoms stream. The acetonitrile product stream may comprise greater than 98 wt %, e.g., greater than 99.5 wt %, acetonitrile and/or less than 1 wt. % methanol. The first column may comprise at least 30 trays, and may comprise a condenser that may use chilled water. The purifying step may comprise the step of treating the first intermediate acetonitrile stream comprising acetonitrile, oxazole, and hydrogen cyanide to produce a second intermediate acetonitrile stream comprising less than 1 wt % acrylonitrile and less than 1 wt % hydrogen cyanide; distilling the second intermediate acetonitrile stream to produce a third distillate comprising acetonitrile, less than 50 wt % water and greater than 0.1 wt % oxazole; and a third bottoms comprising greater than 90 wt % acetonitrile and allyl alcohol; distilling the third bottoms to produce: a fourth distillate comprising greater than 95 wt % acetonitrile; and a fourth bottoms comprising greater than 1 wt % allyl alcohol and greater than 5 wt % propionitrile; and treating the fourth distillate in a resin bed to remove oxazole.

In some embodiments, a process for producing acetonitrile, the process comprising treating a feedstock stream comprising methanol, allyl alcohol, oxazole, acetonitrile, water, and hydrogen cyanide to remove hydrogen cyanide and produce an acetonitrile stream comprising less than 1 wt. % hydrogen cyanide, distilling the acetonitrile stream in a first distillation column to yield at least a first intermediate acetonitrile stream comprising acetonitrile and oxazole and less than 1 wt % allyl alcohol; treating the first intermediate acetonitrile stream to produce a second intermediate acetonitrile stream comprising less than 1 wt % acrylonitrile and less than 1 wt % hydrogen cyanide; and distilling the second intermediate acetonitrile stream to produce a third distillate comprising acetonitrile, less than 50 wt % water and greater than 0.1 wt % oxazole; and a third bottoms comprising greater than 90 wt % acetonitrile and allyl alcohol. In one embodiment, the first intermediate acetonitrile stream is a sidedraw and may be taken in the upper 70% of the first distillation column. In one embodiment, the third bottoms comprises greater than 98 wt % acetonitrile. In some embodiments, the process further comprises distilling the third bottoms to produce a fourth distillate comprising greater than 95 wt % acetonitrile; and a fourth bottoms comprising greater than 1 wt % allyl alcohol and greater than 5 wt % propionitrile. In some embodiments, the fourth distillate comprises greater than 98 wt % acetonitrile.

BRIEF DESCRIPTION OF THE DRAWINGS

FIGURE is a schematic of a separation scheme for acrylonitrile production and purification process in accordance with one embodiment of the invention.

DETAILED DESCRIPTION

As noted above, conventional acrylonitrile production process waste streams contain amounts of desirable co-products, e.g., acetonitrile, which may be recovered and/or purified to yield saleable (acetonitrile) product. The inventors have found that, in some cases, the acetonitrile-containing waste streams may comprise other impurities, e.g., methanol, which were not previously contemplated in separation schemes. In some cases, it has been discovered that methanol may be employed in acrylonitrile reactors to favor the production of hydrogen cyanide, which, in turn, may contribute to process efficiencies. This methanol may then carry through to the remainder of the production process and ultimately be present in the acrylonitrile waste streams. Methanol, regardless of the source and even in small amounts, has been found to create significant problems in the separation and/or purification of the by-product acetonitrile. As one example, it has been found that methanol has the ability to detrimentally azeotrope with the by-product acetonitrile, thus resulting in separation inefficiencies, poor final purity levels, and low yields. Conventional acetonitrile recovery processes provide little or no guidance relating to effective separation of feedstock streams that comprise methanol.

In addition, the separation of other co-products, e.g., allyl alcohol, hydrogen cyanide, and oxazole, has conventionally required a series of multiple units, e.g., multiple columns, to achieve a suitable separation. And still, the separation may not yield a highly pure acetonitrile product.

The acetonitrile-containing waste streams disclosed herein may comprise further impurities, e.g., propionitrile. Propionitrile may be present as an additional co-product of conventional acrylonitrile production processes and has also been found to create significant problems in the separation and/or purification of the by-product acetonitrile. Conventional methods of separation and/or purification of the co-product acetonitrile provide little or no guidance relating to effective propionitrile separation. As a result, the propionitrile may remain present in the final product of these conventional methods, resulting in poor final purity levels and low yields.

The separation of particular waste streams using the specific separation schemes (disclosed herein) advantageously results in significant quantities of high purity acetonitrile product. In particular, the use of, inter alia, a digester-column-digester configuration provides for an improved-efficiency separation that yields the high purity acetonitrile product stream and also alleviates separation burden on downstream units and provides for cost benefits. Without being bound by theory, it is believed that the digester-column-digester configuration surprisingly minimizes caustic use, while achieving suitable (improved) contaminant digestion. In some cases, known problems relating to acrylonitrile treatment are minimized or eliminated. In some embodiments, the operation of the distillation (optionally with the digester configurations) as described herein, provides for the use of a single column, as opposed to multiple columns, as required in conventional separation schemes. In some cases, it has been found that treatment of the feedstock to remove hydrogen cyanide (HCN) prior to downstream separation, e.g., distillation (as described herein), leads to significant distillation efficiencies. It is believed that HCN removal prior to distillation provides for column efficiencies, which in turn allows for reductions in column capital expense, e.g., operation with fewer trays.

Further, the separation of methanol early in the separation scheme, e.g., prior to final acetonitrile purification, beneficially, prevents methanol build-up in the downstream separation units. This reduction or elimination of methanol, in turn, leads to a reduction or elimination of methanol-acetonitrile azeotrope, which advantageously reduces the need for complex separation processes to break the azeotrope and further separate the components. Further, the inventors have discovered that the aforementioned methanol removal contributes to unexpected efficiencies in (downstream) propionitrile separation, e.g., in a column configured downstream of the pressure swing distillation system.

The present disclosure relates to a process for producing a high-purity acetonitrile product from a low-purity acetonitrile feedstock that contains methanol. The process comprises the step of treating a feedstock comprising, among others, HCN, to remove HCN and produce an acetonitrile stream, e.g., comprising less than 1 wt. % HCN. The feedstock may comprise multiple co-products, which complicate separation. Some of these co-products include allyl alcohol, oxazole, methanol, and water. The composition of the feedstock is discussed in more detail below.

The process further comprises the step of distilling the acetonitrile stream in a first column to produce a first distillate, a first intermediate acetonitrile stream, and a first bottoms stream. The step is conducted such that the first distillate comprises significant portions of oxazole and methanol; the first intermediate acetonitrile stream comprises acetonitrile and oxazole and less than 1 wt % allyl alcohol; and the first bottoms stream comprises allyl alcohol and water. Distillation in this manner (under conditions disclosed herein) has been found to remove significant quantities of methanol and oxazole (as a distillate) and water and allyl alcohol (as bottoms), which provides for an improved-efficiency separation and also alleviates separation burden on downstream units. In some cases, the first distillation column is operated at a pressure greater than vacuum. In some embodiments, the (bulk of the) separation of the methanol and the oxazole and of the water and allyl alcohol are achieved in the first column alone, e.g., not in multiple columns, which advantageously improves overall separation operation as well as reduces capital investment. The process further comprises the step of purifying the first intermediate acetonitrile stream to produce a (high purity) acetonitrile product stream and a recycle stream comprising allyl alcohol (optionally in lesser amounts/concentrations due to previous allyl alcohol removal in the first distillation step). The high purity acetonitrile product stream may comprise greater than 98 wt % acetonitrile, e.g., greater than 99 wt %, greater than 99.5 wt %, greater than 99.7 wt %, greater than 99.9 wt %, greater than 99.92 wt %, greater than 99.95 wt %, or greater than 99.97 wt %. The concentration of acetonitrile in the high purity acetonitrile product may range, for example, from 98 wt % to 99.99 wt %, e.g., from 98 wt % to 99.92 wt %, from 98.82 wt % to 99.95 wt %, from 99.31 wt % to 99.97 wt %, from 99.59 wt % to 99.98 wt %, or from 99.76 wt % to 99.99 wt %.

In some cases, the distillation is conducted such that:
the first distillate comprises greater than 1 wt % oxazole and/or greater than 5 wt % methanol;
the first intermediate acetonitrile stream comprises greater than 25 wt % acetonitrile, less than 5 wt % oxazole, and/or less than 50 wt % water; and/or
the first bottoms stream comprises greater than 0.01 wt % allyl alcohol and greater than 75 wt % water.

Additional concentration ranges and limits for the components (and other components) of these streams are provided herein.

In some embodiments, the recycle stream comprise a smaller amount of allyl alcohol than the first bottoms stream, which has been found to be beneficial because a significant portion of the allyl alcohol is not required to be carried through the separation chain, rather it is effectively removed far upstream. For example, the recycle stream may have at least 1% less concentration of allyl alcohol than the first bottoms stream, e.g., at least 10% less, at least 5% less, at least 20% less, at least 25% less, at least 30% less, at least 40% less, at least 50% less, at least 75% less, or at least 95% less.

In some embodiments, the first intermediate acetonitrile stream is taken from the first column as a sidedraw. In some cases, the sidedraw is taken from above the $10^{th}$ tray of the column, e.g., above the $15^{th}$ tray, above the $20^{th}$ tray, above the $25^{th}$ tray, or above the $30^{th}$ tray. In one embodiment, the sidedraw is taken from the upper 75% of the trays of the column, e.g., the upper 70%, the upper 60%, the upper 50%, the upper 40%, or the upper 30%. Without being bound by theory, it is believed that the acrylonitrile separation peak is present in the upper portion of the column, thus, removing the sidedraw from the upper portion may lead to the aforementioned improvements. And the inventors have found that removing a higher acetonitrile content stream improves subsequent separation.

The first column may comprise at least 30 trays, e.g., at least 33 trays, at least 35 trays, at least 37 trays, at least 40 trays, at least 42 trays, at least 45 trays, at least 47 trays, or at least 50 trays. The inventors have found that by using a column having this number of trays, effective separation of methanol, oxazole, water, and allyl alcohol may be advantageously achieved in a single operation. The first column may operate at the temperatures and pressures disclosed herein. In some cases, the first column comprises a condenser, and the condenser employs chilled water, e.g., from $-5°$ C. to $25°$ C., as a cooling medium.

In some cases, the purifying comprises the step of treating the first intermediate acetonitrile stream to remove acrylonitrile and produce a second intermediate acetonitrile stream comprising less than 1 wt % acrylonitrile and less than 1 wt % HCN. As disclosed herein, the aforementioned first distillation allows for improved efficiency in the treatment of the resultant intermediate acetonitrile stream. The first intermediate acetonitrile stream may initially comprise acrylonitrile, acetonitrile, oxazole, and HCN. The concentrations of the components of the first intermediate acetonitrile stream are disclosed in more detail herein.

Feedstock

As noted above, the present process addresses the presence of many co-products, e.g., allyl alcohol, oxazole, and methanol, in the feedstock and provides for effective separation resulting in a highly pure acetonitrile product.

The process of the present disclosure may begin with a specific feedstock stream, e.g., comprising inter alia allyl alcohol and/or methanol. In some cases, oxazole may also be present, and the oxazole may further complicate separation, due to its chemical structure and physical properties. The feedstock comprises (low amounts of) acetonitrile and methanol, as well as optional components such as HCN, acrylonitrile, and (significant amounts) water. In some embodiments, the feedstock stream may be one or more waste streams of another industrial chemical production processes, e.g., the production of acrylonitrile, allyl cyanide, butyronitrile, polyacrylonitrile, polyamides, polyaramids, or combinations thereof. For example, the feedstock stream may comprise one or more waste streams from such processes. In a specific case, the feedstock stream may be one or more waste streams, e.g., purge streams, from an acrylonitrile production process. For example, waste streams from multiple processes for producing organic nitriles or derivatives thereof may be combined to form the feedstock stream.

In conventional processes, acetonitrile-containing waste streams of acrylonitrile production processes are burned in waste heat boilers to suppress the formation of nitrogen oxides. This solution, however, fails to capture the by-product acetonitrile. In the processes of the present disclosure, however, these waste streams may be processed to recover the acetonitrile, preferably in at a high purity level.

The feedstock stream of the present disclosure comprises acetonitrile. In some embodiments, the feedstock stream comprises a relatively low content of acetonitrile. In one embodiment, the feedstock comprises acetonitrile in an amount ranging from 0.05 wt. % to 50.0 wt. %, based on the total weight of the feedstock stream, e.g., from 0.05 wt. % to 35 wt. %, from 0.1 wt. % to 35 wt. %, from 0.5 wt. % to 25 wt. %, from 1 wt. % to 20 wt. %, from 2 wt. % to 18 wt. %, from 3 wt. % to 16 wt. %, or from 5 wt. % to 15 wt. %. In terms of upper limits, the feedstock stream may comprise less than 50 wt. % acetonitrile, e.g., less than 40 wt. %, less than 35 wt %, less than 30 wt. %, less than 25 wt. %, less than 20 wt. %, less than 18 wt. %, less than 16 wt. %, less than 15 wt. %, less than 12 wt. %, or less than 10 wt. %. In terms of lower limits, the feedstock stream may comprise greater than 0.05 wt. % acetonitrile, e.g., greater than 0.1 wt. %, greater than 0.5 wt. %, greater than 1 wt. %, greater than 2 wt. %, or greater than 5 wt. %.

Generally, as used herein, the weight percentages are based on the total weight of the respective stream. With respect to the feedstock, the weight percentages include all components of the feedstock, including a significant portion of water. In some embodiments, for example, the feedstock comprises greater than 50 wt. % water, e.g., greater than 60 wt. %, greater than 70 wt. %, greater than 75 wt. %, or greater than 80 wt. %. It is contemplated that a feed stream comprising less water, e.g., a partially dehydrated or fully dehydrated feed stream, may be employed. In such a case, the component percentages discussed herein could easily be recalculated/derived by starting with the aforementioned component percentages and recalculating based on a lesser amount of water, e.g., taking water out of the basis for the weight percent calculation.

The feedstock stream also comprises methanol. In one embodiment, the feedstock comprises methanol in an amount ranging from 0.01 wt. % to 10 wt. %, e.g., from 0.1 wt. % to 8 wt. %, from 0.5 wt. % to 7 wt. %, from 1 wt. % to 7 wt. %, from 0.01 wt. % to 3 wt. %, from 0.01 wt. % to 1 wt. %, from 0.05 wt. % to 1 wt. %, from 0.01 wt. % to 0.5 wt. %, from 0.01 wt. % to 0.3 wt. %, from 0.05 wt. % to 1 wt. %, from 0.05 wt. % to 0.5 wt. %, from 0.05 wt. % to 0.3 wt. %, from 0.075 wt. % to 1 wt. %, from 0.075 wt. % to 0.5 wt. %, or from 0.075 wt. % to 0.3 wt. %. In terms of upper limits, the feedstock stream may comprise less than 10 wt.

% methanol, e.g., less than 9 wt. %, less than 8 wt. %, less than 7 wt. %, less than 6 wt. %, less than 5 wt. %, less than 4 wt. %, less than 3 wt. %, less than 2 wt. %, less than 1 wt. %, less than 0.5 wt. %, or less than 0.3 wt. %. In terms of lower limits, the feedstock stream may comprise greater than 0.01 wt. % methanol, e.g., greater than 0.05 wt. %, greater than 0.075 wt. %, greater than 0.1 wt. %, greater than 0.5 wt. %, greater than 1 wt. %, or greater than 2 wt. %.

The feedstock stream may further comprise propionitrile. In one embodiment, the feedstock comprises propionitrile in an amount ranging from 0.01 wt. % to 1 wt. %, e.g., from 0.01 wt. % to 0.5 wt. %, from 0.01 wt. % to 0.3 wt. %, from 0.05 wt. % to 1 wt. %, from 0.05 wt. % to 0.5 wt. %, from 0.05 wt. % to 0.3 wt. %, from 0.075 wt. % to 1 wt. %, from 0.075 wt. % to 0.5 wt. %, or from 0.075 wt. % to 0.3 wt. %. In terms of upper limits, the feedstock stream may comprise less than 1 wt. % propionitrile, e.g., less than 0.5 wt. %, or less than 0.3 wt. %. In terms of lower limits, the feedstock stream may comprise greater than 0.01 wt. % propionitrile, e.g., greater than 0.05 wt. %, or greater than 0.075 wt. %.

The feedstock stream may also comprise oxazole. In one embodiment, the feedstock comprises oxazole in an amount ranging from 0.01 wt. % to 1 wt. %, e.g., from 0.01 wt. % to 0.5 wt. %, from 0.01 wt. % to 0.3 wt. %, from 0.01 wt. % to 0.1 wt. %, from 0.05 wt. % to 1 wt. %, from 0.05 wt. % to 0.5 wt. %, from 0.05 wt. % to 0.3 wt. %, from 0.05 wt. % to 0.1 wt. %, from 0.075 wt. % to 1 wt. %, from 0.075 wt. % to 0.5 wt. %, from 0.075 wt. % to 0.3 wt. %, or 0.075 wt. % to 0.1 wt. %. In terms of upper limits, the feedstock stream may comprise less than 1 wt. % oxazole, e.g., less than 0.5 wt. %, less than 0.3 wt. %, or less than 0.1 wt. %. In terms of lower limits, the feedstock stream may comprise greater than 0.01 wt. % oxazole, e.g., greater than 0.05 wt. %, or greater than 0.075 wt. %.

In some embodiments, the feedstock stream also comprises HCN. In one embodiment, the feedstock comprises HCN in an amount ranging from 0.01 wt. % to 2 wt. %, e.g., from 0.01 wt. % to 1 wt. %, from 0.01 wt. % to 0.5 wt. %, from 0.01 wt. % to 0.3 wt. %, from 0.05 wt. % to 2 wt. %, from 0.05 wt. % to 1 wt. %, from 0.05 wt. % to 0.5 wt. %, from 0.05, to 0.3 wt. %, from 0.075 wt. % to 2 wt. %, from 0.075 wt. % to 1 wt. %, from 0.075 to 0.5 wt. %, from 0.075 wt. % to 0.3 wt. % from 0.1 wt. % to 2 wt. %, from 0.1 wt. % to 1 wt. %, from 0.1 wt. % to 0.5 wt. %, or from 0.1 wt. % to 0.5 wt. %. In terms of upper limits, the feedstock stream may comprise less than 2 wt. % HCN, e.g., less than 1 wt. %, less than 0.5 wt. %, or less than 0.3 wt. %. In terms of lower limits, the feedstock stream may comprise greater than 0.01 wt. % HCN, e.g., greater than 0.05 wt. %, greater than 0.075 wt. %, or greater than 0.1 wt. %.

In one embodiment, the feedstock stream comprises HCN in an amount ranging from 0.01 wt. % to 10 wt. %, e.g., from 0.01 wt. % to 5 wt. %, from 0.01 to 2 wt. %, from 0.1 wt. % to 10 wt. %, from 0.1 wt. % to 5 wt. %, from 0.1 wt. % to 2 wt. %, from 0.5 wt. % to 10 wt. %, from 0.5 wt. % to 5 wt. %, from 0.5 wt. % to 2 wt. %, from 1 wt. % to 10 wt. %, from 1 wt. % to 5 wt. %, or from 1 wt. % to 2 wt. %. In terms of upper limits, the feedstock stream may comprise less than 10 wt. % of HCN, e.g., less than 5 wt. %, or less than 2 wt. %. In terms of lower limit, the feedstock stream may comprise greater than 0.01 wt. % hydrogen cyanide, e.g., greater than 0.1 wt. %, greater than 0.5 wt. %, and greater than 1 wt. %.

The feedstock stream may also comprise allyl alcohol. In one embodiment, the feedstock comprises allyl alcohol in an amount ranging from 0.01 wt. % to 1 wt. %, e.g., from 0.01 wt. % to 0.5 wt. %, from 0.01 wt. % to 0.3 wt. %, from 0.01 wt. % to 0.1 wt. %, from 0.05 wt. % to 1 wt. %, from 0.05 wt. % to 0.5 wt. %, from 0.05 wt. % to 0.3 wt. %, from 0.05 wt. % to 0.1 wt. %, from 0.075 wt. % to 1 wt. %, from 0.075 wt. % to 0.5 wt. %, from 0.075 wt. % to 0.3 wt. %, or 0.075 wt. % to 0.1 wt. %. In terms of upper limits, the feedstock stream may comprise less than 1 wt. % allyl alcohol, e.g., less than 0.5 wt. %, less than 0.3 wt. %, or less than 0.1 wt. %. In terms of lower limits, the feedstock stream may comprise greater than 0.01 wt. % allyl alcohol, e.g., greater than 0.05 wt. %, or greater than 0.075 wt. %.

The feedstock stream may also comprise acrylonitrile. In one embodiment, the feedstock comprises acrylonitrile in an amount ranging from 0.01 wt. % to 1 wt. %, e.g., from 0.01 wt. % to 0.5 wt. %, from 0.01 wt. % to 0.3 wt. %, from 0.01 wt. % to 0.1 wt. %, from 0.05 wt. % to 1 wt. %, from 0.05 wt. % to 0.5 wt. %, from 0.05 wt. % to 0.3 wt. %, from 0.05 wt. % to 0.1 wt. %, from 0.075 wt. % to 1 wt. %, from 0.075 wt. % to 0.5 wt. %, from 0.075 wt. % to 0.3 wt. %, or 0.075 wt. % to 0.1 wt. %. In terms of upper limits, the feedstock stream may comprise less than 1 wt. % acrylonitrile, e.g., less than 0.5 wt. %, less than 0.3 wt. %, or less than 0.1 wt. %. In terms of lower limits, the feedstock stream may comprise greater than 0.01 wt. % acrylonitrile, e.g., greater than 0.05 wt. %, or greater than 0.075 wt. %.

The feedstock stream of the present disclosure may also comprise various impurities, typically in small amounts, e.g., ppm or ppb. These impurities may include various waste products that result from the production of organic nitriles and derivatives thereof. For example, the feedstock stream may comprise acrylamides, azoles, aliphatic nitriles, aromatic nitriles, alcohols, aldehydes, acrolein, fumarin, acrylamide, and cyanide salts.

HCN Treatment

As noted above, the feedstock may comprise various impurities, including HCN. In order to remove some of these impurities, particularly hydrogen cyanide, the process comprises the step of treating the feedstock. The treating step yields the acetonitrile stream, which contains little or no HCN. By removing HCN prior to distillation, significant distillation efficiencies are achieved. In some cases, the HCN removal can be advantageously recovered and re-used, thus creating additional efficiencies. As another benefit, the metallurgy of the columns can be reduced—the columns can be constructed of lower performance alloys, which further contributes to reductions in capital expenditure.

In some embodiments, treatment comprises reacting the HCN in the feedstock stream with a caustic solution, which may react with the HCN, thus consuming it. The caustic solution may vary widely. For example the caustic solution may comprise a strong base, especially alkali bases. For example, the caustic solution may comprise sodium hydroxide, potassium hydroxide, magnesium hydroxide, calcium hydroxide, or combinations thereof. In preferred embodiments, the caustic solution is a solution of sodium hydroxide. The caustic solution may also comprise other compounds. For example, the caustic solution may comprise an aldehyde, such as formaldehyde.

In some embodiments, treatment of the feedstock stream occurs in a digester, which may be heated to increase the rate of the treatment reaction. In some embodiments, the digester of the treatment step is operated at a temperature greater than 55° C., e.g., greater than 70° C., greater than 75° C., or greater than 125° C. In terms of upper limits, the digester may be operated at a temperature less than 150° C., e.g., less than 232° C., less than 225° C., or less than 135° C. In terms of ranges, the digester may be operated at a temperature from 55° C. to 150° C., e.g., from 55° C. to 232° C., from 55° C. to 225° C., from 55° C. to 135° C., from 70° C. to 150° C., from 70° C. to 232° C., from 70° C. to 225° C., from 70° C. to 135° C., from 75° C. to 150° C., from 75° C. to 232° C., from 75° C. to 225° C., from 75° C. to 135° C., from 125° C. to 150° C., from 125° C. to 232° C., from 125° C. to 225° C., or from 125° C. to 135° C.

In one embodiment, the feedstock stream comprises HCN in the amounts noted herein. By treating the feedstock stream, some or all of the hydrogen cyanide impurity in the stream may form a salt, which is subsequently separated, recovered, and/or re-used. In one embodiment, the entirety of the hydrogen cyanide content of the feedstock stream may be recovered. In some embodiments, the resulting acetonitrile stream may comprise a relatively low amount of hydrogen cyanide. In one embodiment, the acetonitrile stream comprises hydrogen cyanide in an amount ranging from 0 wt. % to 0.1 wt. %, e.g., from 0 wt. % to 0.05 wt. %, from 0 wt. % to 0.01 wt. %, from 0 wt. % to 0.005 wt. %, from 0 wt. % to 0.001 wt. %, from 0.0001 wt. % to 0.1 wt. %, from 0.0001 wt. % to 0.05 wt. %, from 0.0001 wt. % to 0.01 wt. %, from 0.0001 wt. % to 0.005 wt. %, from 0.0001 wt. % to 0.001 wt. %, from 0.00005 wt. % to 0.1 wt. %, from 0.00005 wt. % to 0.05 wt. %, from 0.00005 wt. % to 0.01 wt. %, from 0.00005 wt. % to 0.005 wt. %, from 0.00005 wt. % to 0.001 wt. %. In terms of upper limits, the acetonitrile stream may comprise less than 0.1 wt. % hydrogen cyanide, e.g., less than 0.05 wt. %, less than 0.01 wt. %, less than 0.005 wt. %, and less than 0.001 wt. %. In terms of lower limits, the acetonitrile stream may comprise greater than 0 wt. % hydrogen cyanide, e.g., greater than 0.00005 wt. %, or greater than 0.0001 wt. %.

The acetonitrile stream comprises other impurities, such as oxazole, that must be removed. In one embodiment, the intermediate acetonitrile stream comprises oxazole in an amount ranging from 0.05 wt. % to 5 wt. %, e.g., from 0.1 wt. % to 4 wt. %, from 0.1 wt. % to 3 wt. %, from 0.1 wt. % to 2 wt. %, from 0.2 wt. % to 5 wt. %, from 0.2 wt. % to 4 wt. %, from 0.2 wt. % to 3 wt. %, from 0.2 wt. % to 2 wt. %. from 0.5 wt. % to 5 wt. %, from 0.5 wt. % to 4 wt. %, from 0.5 wt. % to 3 wt. %, from 0.5 wt. % to 2 wt. %, from 1 wt. % to 5 wt. %, from 1 wt. % to 4 wt. %, from 1 wt. % to 3 wt. %, or from 1 wt. % to 2 wt. %. In terms of upper limits, the intermediate acetonitrile stream may comprise less than 5 wt. % oxazole, e.g., less than 4 wt. %, less than 3 wt. %, or less than 2 wt. %. In terms of lower limits, the intermediate acetonitrile stream may comprise greater than 0.05 wt. %, e.g., greater than 0.1 wt. %, greater than 0.2 wt. %, greater than 0.5 wt. %, or greater than 1 wt. %.

First Distillation

As noted above, the acetonitrile stream is distilled in a first distillation column to yield a first intermediate acetonitrile stream. The first distillation, in some cases, removes a significant portion (if not all) of oxazole, methanol, allyl alcohol, and water in the acetonitrile stream.

The structure of the first distillation column may vary widely. And various distillation columns are known to those of ordinary skill in the art, and any suitable column may be employed as long as the aforementioned separation is achieved. For example the first distillation column may comprise any suitable separation device or combination of separation devices. For example, the first distillation column may comprise a column, e.g., a standard distillation column, an extractive distillation column and/or an azeotropic distillation column. In some cases, the term "first distillation column" may refer to multiple distillation columns configured with one another.

In some embodiments, the first distillation column operates at a pressure ranging from 100 kPa to 175 kPa, e.g., from 100 kPa to 165 kPa, from 100 kPa to 160 kPa, from 100 kPa to 150 kPa, from 100 kPa to 145 kPa, from 105 kPa to 175 kPa, from 105 kPa to 165 kPa, from 105 kPa to 160 kPa, from 105 kPa to 150 kPa, from 105 kPa to 145 kPa, from 110 kPa to 175 kPa, from 110 kPa to 165 kPa, from 110 kPa to 160 kPa, from 110 kPa to 150 kPa, from 110 kPa to 145 kPa, from 115 kPa to 175 kPa, from 115 kPa to 165 kPa, from 115 kPa to 160 kPa, from 115 kPa to 150 kPa, from 115 kPa to 145 kPa, from 120 kPa to 175 kPa, from 120 kPa to 165 kPa, from 120 kPa to 160 kPa, from 120 kPa to 150 kPa, or from 120 kPa to 145 kPa. In terms of lower limits, the first distillation column may operate at a pressure greater than 100 kPa, e.g., greater than 105 kPa, greater than 110 kPa, greater than 115 kPa, or greater than 120 kPa. In terms of upper limits, the first distillation column may operate at a pressure less than 175 kPa, e.g., less than 165 kPa, less than 160 kPa, less than 150 kPa, or less than 145 kPa.

In some embodiments, the first distillation column operates at a temperature ranging from 50° C. to 135° C., e.g., from 50° C. to 130° C., from 50° C. to 125° C., from 50° C. to 115° C., from 55° C. to 135° C., from 55° C. to 130° C., from 55° C. to 125° C., from 55° C. to 115° C., from 60° C. to 135° C., from 60° C. to 130° C., from 60° C. to 125° C., from 60° C. to 115° C., from 55° C. to 135° C., from 55° C. to 130° C., from 55° C. to 125° C., or from 55° C. to 115° C. In terms of lower limits, the first distillation column may operate a temperature greater than 50° C., e.g., greater than 55° C., greater than 60° C., or greater than 55° C. In terms of upper limits, the first distillation column may operate a temperature less than 135° C., e.g., less than 130° C., less than 125° C., or less than 115° C.

In some cases, the first distillate comprises greater than 1 wt % oxazole, e.g., greater than 3 wt. %, greater than 5 wt. %, or greater than 7 wt. %. In terms of ranges, the first distillate may comprise from 0.1 wt. % to 20 wt. % oxazole, e.g., from 0.5 wt. % to 15 wt. %, from 1 wt. % to 12 wt. %, or from 3 wt. % to 12 wt. %. In terms of upper limits, the first distillate may comprise less than 20 wt. % oxazole, e.g., less than 15 wt. %, less than 12 wt. %, or less than 10 wt. %.

In some embodiments, the first distillate may comprise methanol in amounts similar to oxazole.

In some cases, the first intermediate acetonitrile stream comprises greater than 25 wt % acetonitrile, e.g., greater than 50 wt. %, greater than 60 wt. %, greater than 70 wt %, or greater than 75 wt. %. In terms of ranges, the first intermediate acetonitrile stream may comprise from 50 wt. % to 99 wt. % acetonitrile, e.g., from 60 wt. % to 90 wt. %, from 70 wt. % to 85 wt. %, or from 70 wt. % to 80 wt. %. In terms of upper limits, the first intermediate acetonitrile stream may comprise less than 99 wt. % acetonitrile, e.g., less than 90 wt. %, less than 85 wt. %, or less than 80 wt. %.

The first intermediate acetonitrile stream may comprise less than 10 wt % oxazole, e.g., less than 5 wt. %, less than 4 wt. %, or less than 3 wt. %. In terms of ranges, the first intermediate acetonitrile stream may comprise from 0.1 wt. % to 10 wt. % oxazole, e.g., from 0.5 wt. % to 8 wt. %, from 0.5 wt. % to 5 wt. %, or from 1 wt. % to 3 wt. %. In terms of lower limits, the first intermediate acetonitrile stream may comprise greater than 0.1 wt % oxazole, e.g., greater than 0.5 wt. %, greater than 0.7 wt. %, or greater than 1 wt. %.

The first intermediate acetonitrile stream may comprise less than 50 wt % water, e.g., less than 40 wt. %, less than 30 wt. %, or less than 25 wt. %. In terms of ranges, the first intermediate acetonitrile stream may comprise from 0.1 wt. % to 50 wt. % water, e.g., from 1 wt. % to 40 wt. %, from 5 wt. % to 30 wt. %, or from 10 wt. % to 25 wt. %. In terms of lower limits, the first intermediate acetonitrile stream may comprise greater than 0.1 wt % water, e.g., greater than 1 wt. %, greater than 5 wt. %, or greater than 10 wt. %.

In some cases, the first bottoms stream comprises greater than 0.01 wt % allyl alcohol, e.g., greater than 0.02 wt. %, greater than 0.03 wt. %, or greater than 0.05 wt. %. In terms of ranges, the first bottoms stream may comprise from 0.001 wt. % to 1 wt. % allyl alcohol, e.g., from 0.005 wt. % to 0.5 wt. %, from 0.005 wt. % to 0.1 wt. %, or from 0.01 wt. % to 0.1 wt. %. In terms of upper limits, the first bottoms stream may comprise less than 1 wt. % allyl alcohol, e.g., less than 0.5 wt. %, less than 0.1 wt. %, or less than 0.08 wt. %.

In some cases, the first bottoms stream comprises greater than 75 wt % water, e.g., greater than 80 wt. %, greater than 85 wt. %, greater than 90 wt %, or greater than 95 wt. %. In terms of ranges, the first bottoms stream may comprise from 75 wt. % to 99 wt. % water, e.g., from 80 wt. % to 99 wt. %, from 85 wt. % to 99 wt. %, or from 90 wt. % to 98.5 wt. %. In terms of upper limits, the first bottoms stream may comprise less than 99 wt. % water, e.g., less than 98.5 wt. %, less than 98 wt. %, or less than 97.5 wt. %.

AN Treatment

As noted above, the first intermediate acetonitrile stream may comprise various impurities, including acrylonitrile. Some of these impurities may remain present in the intermediate acetonitrile stream after the distillation in the first distillation column. In order to remove some of these impurities, particularly acrylonitrile, the process comprises the step of treating the intermediate acetonitrile stream to remove, inter alia, acrylonitrile. This treating step yields a second intermediate acetonitrile stream comprising little or no acrylonitrile, e.g., less than 1 wt. % acrylonitrile, and optionally less than 1 wt % hydrogen cyanide. The removal of the AN in this step is made easier by the upstream operations because the HCN has already been removed in the first treatment step.

In some embodiments, treatment of the first intermediate acetonitrile stream comprises reacting the first intermediate acetonitrile stream with a caustic solution, which may react with the acrylonitrile, thus consuming acrylonitrile in the crude acetonitrile stream. The treatment of the first intermediate acetonitrile stream may be conducted in a manner similar to that of the treatment of the feedstock stream (discussed above). In some cases, less caustic treatment is required because little or no HCN is present to use up the caustic—the majority or all of the caustic can be used to remove acrylonitrile. In some cases, the process uses less caustic in the second digester than in the first digester.

In one embodiment, the first intermediate acetonitrile stream comprises acrylonitrile in an amount ranging from 0.01 wt. % to 10 wt. %, e.g., from 0.01 wt. % to 5 wt. %, from 0.01 to 2 wt. %, from 0.05 wt. % to 5 wt. %, from 0.05 wt. % to 3 wt. %, or from 0.05 wt. % to 2 wt. %. In terms of upper limits, the first intermediate acetonitrile stream may comprise less than 10 wt. % of acrylonitrile, e.g., less than 5 wt. %, less than 3 wt. %, less than 2 wt. %, less than 1 wt. %, or less than 0.5 wt. %. In terms of lower limit, the first intermediate acetonitrile stream may comprise greater than 0.01 wt. % acrylonitrile, e.g., greater than 0.05 wt. %, greater than 0.07 wt. %, or greater than 0.09 wt. %.

By treating the first intermediate acetonitrile stream, some or all of the (remaining) acrylonitrile impurity in the stream may be consumed. In one embodiment, the entirety of the acrylonitrile content of the first intermediate acetonitrile stream may be consumed. In some embodiments, the resulting second intermediate acetonitrile stream may comprise a relatively low amount of acrylonitrile.

In one embodiment, the second intermediate acetonitrile stream comprises acrylonitrile in an amount ranging from 0 wt. % to 0.1 wt. %, e.g., from 0 wt. % to 0.05 wt. %, from 0 wt. % to 0.01 wt. %, from 0 wt. % to 0.005 wt. %, from 0 wt. % to 0.001 wt. %, from 0.0001 wt. % to 0.1 wt. %, from 0.0001 wt. % to 0.05 wt. %, from 0.0001 wt. % to 0.01 wt. %, from 0.0001 wt. % to 0.005 wt. %, from 0.0001 wt. % to 0.001 wt. %, from 0.00005 wt. % to 0.1 wt. %, from 0.00005 wt. % to 0.05 wt. %, from 0.00005 wt. % to 0.01 wt. %, from 0.00005 wt. % to 0.005 wt. %, from 0.00005 wt. % to 0.001 wt. %. In terms of upper limits, the second intermediate acetonitrile stream may comprise less than 0.1 wt. % acrylonitrile, e.g., less than 0.05 wt. %, less than 0.01 wt. %, less than 0.005 wt. %, and less than 0.001 wt. %. In terms of lower limits, the second intermediate acetonitrile stream may comprise greater than 0 wt. % acrylonitrile, e.g., greater than 0.00005 wt. %, or greater than 0.0001 wt. %.

Second Distillation

The second intermediate acetonitrile stream may be purified in one or more columns to produce a third distillate and a third bottoms. The third bottoms comprises a relatively high amount of acetonitrile and may be considered an acetonitrile product stream.

In some embodiments, the third distillate comprises greater than 50 wt. % acetonitrile, e.g., greater than 55 wt. %, greater than 60 wt. %, greater than 65 wt. %, or greater than 70 wt. %. In terms of ranges, the third distillate may comprise from 50 wt. % to 95 wt. % acetonitrile, e.g., from 55 wt. % to 90 wt. %, from 60 wt. % to 85 wt. %, from 65 wt. % to 85 wt. %, or from 70 wt. % to 80 wt. %. In terms of lower limits, the third distillate may comprise less than 95 wt. % acetonitrile, e.g., less than 90 wt. %, less than 85 wt. %, less than 80 wt. %, or less than 75 wt. %.

In some embodiments, the third distillate may comprise less than 50 wt. % water, e.g., less than 40 wt. %, less than 35 wt. %, less than 30 wt. %, or less than 28 wt. %. In terms of ranges, the third distillate may comprise from 1 wt. % to 50 wt. % water, e.g., from 5 wt. % to 40 wt. %, from 10 wt. % to 35 wt. %, from 15 wt. % to 35 wt. %, or from 20 wt. % to 30 wt. %. In terms of lower limits, the third distillate comprises greater than 1 wt. % acetonitrile, e.g., greater than 5 wt. %, greater than 10 wt. %, greater than 15 wt. %, or greater than 20 wt. %.

In some embodiments, the third distillate comprises greater than 0.1 wt. % oxazole, e.g., greater than 0.5 wt. %, greater than 1 wt. %, greater than 1.5 wt. %, or greater than 1.8 wt. %. In terms of ranges, the third distillate may comprise from 0.1 wt. % to 10 wt. % oxazole, e.g., from 0.5 wt. % to 8 wt. %, from 1 wt. % to 5 wt. %, from 1.5 wt. % to 4 wt. %, or from 1.8 wt. % to 3 wt. %. In terms of lower limits, the third distillate may comprise less than 10 wt. % oxazole, e.g., less than 8 wt. %, less than 5 wt. %, less than 4 wt. %, or less than 3 wt. %.

In some cases, the third bottoms comprises greater than 90 wt % acetonitrile, e.g., greater than 92 wt. %, greater than 94 wt. %, greater than 95 wt. %, or greater than 96 wt. %. In terms of ranges, the third bottoms may comprise from 90 wt. % to 99.99 wt. % acetonitrile, e.g., from 92 wt. % to 99.9 wt. %, from 94 wt. % to 99 wt. %, from 95 wt. % to 99 wt. %, or from 96 wt. % to 98 wt. %. In terms of lower limits, the third bottoms may comprise less than 99.9 wt. % acetonitrile, e.g., less than 99.9 wt. %, less than 99 wt. %, or less than 98 wt. %.

In some cases, the third bottoms comprises greater than 0.01 wt % allyl alcohol, e.g., greater than 0.05 wt. %, greater than 0.1 wt. %, greater than 0.2 wt. %, or greater than 0.3 wt. %. In terms of ranges, the third bottoms may comprise from 0.01 wt. % to 10 wt. % allyl alcohol, e.g., from 0.05 wt. % to 5 wt. %, from 0.1 wt. % to 3 wt. %, or from 0.2 wt. % to 1 wt. %. In terms of lower limits, the third bottoms may comprise less than 10 wt. % allyl alcohol, e.g., less than 5 wt. %, less than 3 wt. %, or less than 1 wt. %.

The second distillation may be conducted at conditions similar to those of the first column. Similar equipment may be employed as well.

Third Distillation

As noted above, the third bottoms stream comprises relatively few impurities, e.g., methanol, oxazole, allyl alcohol. In some embodiments, the third bottoms stream comprises a sufficiently high concentration of acetonitrile. As such, it may not be necessary to further purify the third bottoms stream. For example, in some case, an "ACN-grade" acetonitrile product is desired. In such cases, the successful formation of the third bottoms stream (with the accompanying acetonitrile purity) yields is a suitable and valuable commercial product.

Other commercial grades that may be produced by the disclosed process include standard industrial grade, Laboratory Grade, ACS Grade, Chromatography Grade, LC Grade, and UHPLC Grade.

In some embodiments, a higher purity of acetonitrile may be desirable or necessary. As such, the third bottoms stream may be distilled, e.g., in a third distillation column, to yield a fourth distillate and a fourth bottoms stream. The fourth distillate may have a high purity level and may be considered a high purity acetonitrile product stream. Various distillation columns are known to those of ordinary skill in the art, and any such column may be used as the final distillation in the present disclosure. In some cases, the third distillation may be conducted at conditions similar to those of the first column. Similar equipment may be employed as well.

In some embodiments, the third distillation column operates at a pressure ranging from 100 mm Hg to 400 mm Hg, e.g., from 100 mm Hg to 375 mm Hg, from 100 mm Hg to 350 mm Hg, from 100 mm Hg to 325 mm Hg, from 100 mm Hg to 300 mm Hg, from 125 mm Hg to 400 mm Hg, from 125 mm Hg to 375 mm Hg, from 125 mm Hg to 350 mm Hg, from 125 mm Hg to 325 mm Hg, from 125 mm Hg to 300 mm Hg, from 150 mm Hg to 400 mm Hg, from 150 mm Hg to 375 mm Hg, from 150 mm Hg to 350 mm Hg, from 150 mm Hg to 325 mm Hg, from 150 mm Hg to 300 mm Hg, from 175 mm Hg to 400 mm Hg, from 175 mm Hg to 375 mm Hg, from 175 mm Hg to 350 mm Hg, from 175 mm Hg to 325 mm Hg, from 175 mm Hg to 300 mm Hg, from 200 mm Hg to 400 mm Hg, from 200 mm Hg to 375 mm Hg, from 200 mm Hg to 350 mm Hg, from 200 mm Hg to 325 mm Hg, or from 200 mm Hg to 300 mm Hg. In terms of lower limits, the third distillation column may operate at a pressure greater than 100 mm Hg, e.g., greater than 125 mm Hg, greater than 150 mm Hg, greater than 175 mm Hg, or greater than 200 mm Hg. In terms of upper limits, the third distillation column may operate at a pressure less than 400 mm Hg, e.g., less than 375 mm Hg, less than 350 mm Hg, less than 325 mm Hg, or less than 300 mm Hg.

In some embodiments, the third distillation column operates at a temperature ranging from 25° C. to 95° C., e.g., from 25° C. to 125° C., from 25° C. to 75° C., from 25° C. to 70° C., from 32° C. to 95° C., from 32° C. to 125° C., from 32° C. to 75° C., from 32° C. to 70° C., from 35° C. to 95° C., from 35° C. to 125° C., from 35° C. to 75° C., from 35° C. to 70° C., from 37° C. to 95° C., from 37° C. to 125° C., from 37° C. to 75° C., or from 37° C. to 70° C. In terms of lower limits, the third distillation column may operate a temperature greater than 25° C., e.g., greater than 32° C., greater than 35° C., or greater than 37° C. In terms of upper limits, the third distillation column may operate a temperature less than 95° C., e.g., less than 125° C., less than 75° C., or less than 70° C.

In one embodiment, the fourth distillate comprises acetonitrile in an amount ranging from 95 wt. % to 100 wt. %, e.g., from 95 wt. % to 99.999 wt. %, from 95 wt. % to 99.99 wt. %, from 97 wt. % to 100 wt. %, from 97 wt. % to 99.999 wt. %, from 97 wt. % to 99.99 wt. %, from 98 wt. % to 100 wt. %, from 98 wt. % to 99.999 wt. %, from 98 wt. % to 99.99 wt. %, from 99 wt. % to 100 wt. %, from 99 wt. % to 99.99 wt. %, from 99 wt. % to 99.9 wt. %, from 99.9 wt. % to 100 wt. %, from 99.9 wt. % to 99.999 wt. %, or from 99.9 wt. % to 99.99 wt. %. In terms of upper limits, the purified acetonitrile stream may comprise less than 100 wt. % acetonitrile, e.g., less than 99.999 wt. % or less than 99.99. In terms of lower limits, the purified acetonitrile stream may comprise greater than 95 wt. % acetonitrile, e.g., greater than 97 wt. %, greater than 98 wt. %, greater than 99 wt. %, greater than 99.9 wt. %, or greater than 99.99 wt. %.

In one embodiment, the fourth distillate comprises low amounts (if any) propionitrile, e.g., in an amount ranging from 0 wt. % to 0.1 wt. %, e.g., from 0 wt. % to 0.05 wt. %, from 0 wt. % to 0.01 wt. %, from 0 wt. % to 0.005 wt. %, from 0 wt. % to 0.0001 wt. %, from 0.00005 wt. % to 0.1 wt. %, from 0.0005 wt. % to 0.05 wt. %, from 0.00005 wt. % to 0.01 wt. %, from 0.00005 wt. % to 0.005 wt. %, from 0.00005 wt. % to 0.0001 wt. %, from 0.0001 wt. % to 0.1 wt. %, from 0.0001 wt. % to 0.05 wt. %, from 0.0001 wt. % to 0.01 wt. %, or from 0.0001 wt. % to 0.005 wt. %. In terms of upper limits, the fourth distillate may comprise less than 0.1 wt. % propionitrile, e.g., less than 0.05 wt. %, less than 0.01 wt. %, less than 0.005 wt. %, or less than 0.0001 wt. %. In terms of lower limits, the fourth distillate may comprise greater than 0 wt. % propionitrile, e.g., greater than 0.00005 wt. %, or greater than 0.0001 wt. %.

In one embodiment, the fourth distillate comprises low amounts (if any) oxazole, e.g., in an amount ranging from 0 wt. % to 0.1 wt. %, e.g., from 0 wt. % to 0.05 wt. %, from 0 wt. % to 0.01 wt. %, from 0 wt. % to 0.005 wt. %, from 0 wt. % to 0.0001 wt. %, from 0.00005 wt. % to 0.1 wt. %, from 0.0005 wt. % to 0.05 wt. %, from 0.00005 wt. % to 0.01 wt. %, from 0.00005 wt. % to 0.005 wt. %, from 0.00005 wt. % to 0.0001 wt. %, from 0.0001 wt. % to 0.1 wt. %, from 0.0001 wt. % to 0.05 wt. %, from 0.0001 wt. % to 0.01 wt. %, or from 0.0001 wt. % to 0.005 wt. %. In terms of upper limits, the fourth distillate may comprise less than 0.1 wt. % oxazole, e.g., less than 0.05 wt. %, less than 0.01 wt. %, less than 0.005 wt. %, or less than 0.0001 wt. %. In terms of lower limits, the fourth distillate may comprise greater than 0 wt. % oxazole, e.g., greater than 0.00005 wt. %, or greater than 0.0001 wt. %.

In one embodiment, the fourth distillate comprises methanol in an amount ranging from 0 wt. % to 0.5 wt. %, e.g., from 0 wt. % to 0.1 wt. %, from 0 wt. % to 0.05 wt. %, from 0 wt. % to 0.01 wt. %, from 0 wt. % to 0.005 wt. %, from 0 wt. % to 0.0001 wt. %, from 0.00005 wt. % to 0.5 wt. %, from 0.00005 wt. % to 0.1 wt. %, from 0.0005 wt. % to 0.05 wt. %, from 0.00005 wt. % to 0.01 wt. %, from 0.00005 wt. % to 0.005 wt. %, from 0.00005 wt. % to 0.0001 wt. %, from 0.0001 wt. % to 0.5 wt. %, from 0.0001 wt. % to 0.1 wt. %, from 0.0001 wt. % to 0.05 wt. %, from 0.0001 wt. % to 0.01 wt. %, or from 0.0001 wt. % to 0.005 wt. %. In terms of upper limits, the fourth distillate may comprise less than 0.5 wt. % methanol, e.g., less than 0.1 wt. %, less than 0.05 wt. %, less than 0.01 wt. %, less than 0.005 wt. %, or less than 0.0001 wt. %. In terms of lower limits, the fourth distillate may comprise greater than 0 wt. % methanol, e.g., greater than 0.00005 wt. %, or greater than 0.0001 wt. %.

In some embodiments, the fourth bottoms comprises greater than 0.1 wt. % allyl alcohol, e.g., greater than 0.5 wt. %, greater than 1 wt. %, greater than 2 wt. %, greater than 5 wt. %, or greater than 7 wt. %. In terms of ranges, the fourth bottoms may comprise from 0.1 wt. % to 25 wt. % allyl alcohol, e.g., from 0.5 wt. % to 20 wt. %, from 1 wt. % to 15 wt. %, or from 5 wt. % to 15 wt. %. In terms of lower limits, the fourth bottoms may comprise less than 25 wt. % allyl alcohol, e.g., less than 20 wt. %, less than 13 wt. %, or less than 10 wt. %.

In some embodiments, the fourth bottoms comprises greater than 0.1 wt. % propionitrile, e.g., greater than 1 wt. %, greater than 3 wt. %, greater than 5 wt. %, greater than 10 wt. %, or greater than 15 wt. %. In terms of ranges, the fourth bottoms may comprise from 0.1 wt. % to 50 wt. % propionitrile, e.g., from 1 wt. % to 40 wt. %, from 3 wt. % to 35 wt. %, or from 5 wt. % to 25 wt. %. In terms of lower limits, the fourth bottoms may comprise less than 50 wt. % propionitrile, e.g., less than 40 wt. %, less than 35 wt. %, or less than 25 wt. %.

In some embodiments, the purifying comprises: treating the fourth distillate in a resin bed to remove oxazole.

Separation Schemes

Beneficially, the disclosed process utilizes fewer columns than traditional systems, which provides the advantages of reducing complexity and capital cost, among others. In one embodiment, the separation scheme eliminates a column. In some cases the process comprises six distillation columns or fewer, e.g., five columns or fewer, four columns or fewer, three columns or fewer, or two columns or fewer. In some cases, the separation scheme comprises only six columns. In some cases, the separation scheme comprises only five columns. In some cases, the separation scheme comprises only four columns. In some cases, the separation scheme comprises only three columns.

In one embodiment, the separation scheme a purifies a feedstock stream comprising oxazole and propionitrile and produces an intermediate acetonitrile stream comprising less than 0.01 wt. % hydrogen cyanide, an acetonitrile product stream comprising less than 1 wt. % methanol, and a purified acetonitrile product stream comprising at least 99.5 wt. % acetonitrile.

In one embodiment, the acetonitrile product stream comprises less than 1 wt. % methanol, the feedstock stream comprises oxazole and propionitrile, the acetonitrile stream comprises less than 0.01 wt. % hydrogen cyanide, and the acetonitrile product stream comprises at least 99.5 wt. % acetonitrile.

As used herein, "greater than" and "less than" limits may also include the number associated therewith. Stated another way, "greater than" and "less than" may be interpreted as "greater than or equal to" and "less than or equal to." It is contemplated that this language may be subsequently modified in the claims to include "or equal to." For example, "greater than 10" may be interpreted as, and subsequently modified in the claims as "greater than or equal to 10."

It will be appreciated that variants of the above-disclosed and other features and functions, or alternatives thereof, may be combined into many other different systems or applications. Various presently unforeseen or unanticipated alternatives, modifications, variations or improvements therein may be subsequently made by those skilled in the art which are also intended to be encompassed by the following claims or the equivalents thereof.

EXAMPLES

The present disclosure will be better understood in view of the following non-limiting example.

Example 1

FIG. illustrates an exemplary separation scheme 100. As shown in the scheme, feedstock stream 102 was prepared by combining three waste streams from an acrylonitrile production and purification process. Feedstock stream 102 is fed to HCN digester 104, which is fed via caustic feed 106. The composition of feedstock stream 102 is shown in Table 1, and includes acetonitrile, acrylonitrile methanol, hydrogen cyanide, water, allyl alcohol, oxazole, and propionitrile. HCN digester 104 treats feedstock stream 102 to remove hydrogen cyanide and produce acetonitrile stream 108. The composition of acetonitrile stream 108 is shown in Table 1.

Acetonitrile stream 108 is fed to first distillation column 110. Distillation of acetonitrile stream 108 yields first distillate stream 112, first bottoms stream 114 and first intermediate acetonitrile stream 116 (shown as a side draw). First distillate stream 112 comprises oxazole, methanol, and other co-products as shown in Table 1. First bottoms stream 114 comprises allyl alcohol, water, and other co-products as shown in Table 1. First intermediate acetonitrile stream 116 comprises acetonitrile and co-products as shown in Table 1. Due to the operating conditions disclosed herein, first intermediate acetonitrile stream 116 contains a significantly higher concentration of acetonitrile.

First intermediate acetonitrile stream 116 is fed to acrylonitrile digester 118, which is fed via caustic feed 120. Acrylonitrile digester 118 treats first intermediate acetonitrile stream 116 to remove acrylonitrile and produce second intermediate acetonitrile stream 122. The compositions of second intermediate acetonitrile stream 122 is shown in Table 1.

Second intermediate acetonitrile stream 122 is fed to second distillation column 124, which yields third distillate 126 and third bottoms 128, the compositions of which are shown in Table 1. In some cases, third distillate 126 may be recycled upstream and combined with acetonitrile stream 108. Third bottoms stream 128, advantageously has a high acetonitrile concentration (as discussed herein).

Third bottoms stream 128 is fed to third distillation column 130, which yields fourth distillate 132 and fourth bottoms 134, the compositions of which are shown in Table 1 in weight percent. Fourth distillate 132 has a very high acetonitrile concentration. Fourth distillate 132 may be treated to remove oxazole via resin bed 136, thus yielding finished acetonitrile stream 138, having a very high acetonitrile concentration. The composition of the product acetonitrile stream is shown in Table 1 in weight percent.

TABLE 1

Stream compositions streams of FIG. separation process.

| | Pounds/hour | | | | | | | | | |
|---|---|---|---|---|---|---|---|---|---|---|
| Component | 48330 102 | 50120 108 | 2529 112 | 44660 114 | 11910 116 | 11910 122 | 8999 126 | 2921 128 | 2825 132 | 93 134 |
| Hydrogen cyanide | 0.36 | 0 | 0 | Is 0 | 0 | 0 | 0 | 0 | 0 | 0 |
| Methanol | 0.7 | 0.67 | 11.61 | 0.09 | 0.29 | 0.29 | 0.38 | 0 | 0 | 0 |
| Oxazole | 0.44 | 0.38 | 7.41 | 0 | 1.61 | 1.61 | 2.13 | 0 | 0 | 0 |
| Acetonitrile | 9.27 | 8.94 | 64.67 | 0.01 | 78.63 | 78.63 | 72.6 | 96.79 | 99.97 | 0 |
| Acrylonitrile | 0.09 | 0.09 | 1.49 | 0 | 0.1 | 0.03 | 0.07 | 0 | 0 | 0 |
| Allyl Alcohol | 0.07 | 0.07 | 0.03 | 0.06 | 0.09 | 0.09 | 0.01 | 0.32 | 0 | 9.96 |
| Propionitrile | 0.04 | 0.04 | 0.17 | 0 | 0.20 | 0.20 | 0.07 | 0.59 | 0.03 | 17.7 |
| Water | 87.69 | 87.48 | 13.9 | 97.39 | 18.57 | 18.54 | 24.59 | 0 | 0 | 0 |
| Other impurities | Bal. | Bal. | Bal. | Bal. | Bal. | Bal. | Bal. | Bal. 1 | Bal. | Bal. |

As shown, the use of the disclosed separation scheme, e.g. the first column, provides for highly effective separation of significant quantities of methanol and oxazole (in the first distillate) and water and allyl alcohol (in the first bottoms). The side draw comprises surprisingly low concentrations of these co-products. As a result, separation burden on downstream units is alleviated. Importantly, as noted herein, the treatment of the feedstock to remove HCN prior to the first distillation contributed to these significant distillation efficiencies. Table 1 indicates that the HCN removal prior to distillation is shown and this is advantageous to provide for column efficiencies. Also, both the third bottoms (128) and the fourth distillate (132) have a high acetonitrile purity level suitable, for example, use as solvent.

EMBODIMENTS

The following embodiments, among others, are disclosed.

Embodiment 1 is a process for producing acetonitrile, the process comprising: treating a feedstock stream comprising methanol, allyl alcohol, oxazole, acetonitrile, water, and hydrogen cyanide to remove hydrogen cyanide and produce an acetonitrile stream comprising less than 1 wt. % hydrogen cyanide, distilling the acetonitrile stream in a first distillation column to produce: a first distillate comprising oxazole and methanol; a first intermediate acetonitrile stream comprising acetonitrile and oxazole and less than 1 wt % allyl alcohol; a first bottoms stream comprising allyl alcohol, and water; and purifying the first intermediate acetonitrile stream to produce an acetonitrile product stream and a recycle stream comprising allyl alcohol.

Embodiment 2 is an embodiment of embodiment 1, wherein the first distillation column is operated at a pressure ranging from 100 kPa to 175 kPa.

Embodiment 3 is an embodiment of embodiments 1 or 2, wherein the first intermediate acetonitrile stream is a sidedraw, optionally taken in the upper 70% of the column.

Embodiment 4 is an embodiments of embodiments 1-3, wherein: the first distillate comprises greater than 1 wt % oxazole and greater than 5 wt % methanol; the first intermediate acetonitrile stream comprises greater than 25 wt % acetonitrile, less than 5 wt % oxazole, and less than 50 wt % water; the first bottoms stream comprises greater than 0.01 wt % allyl alcohol and greater than 75 wt % water.

Embodiment 5 is an embodiments of embodiments 1-4, wherein the recycle stream comprise a smaller amount of allyl alcohol than the first bottoms stream.

Embodiment 6 is an embodiments of embodiments 1-5, wherein the acetonitrile product stream comprising greater than 98 wt % acetonitrile.

Embodiment 7 is an embodiment of embodiments 1-6, wherein the first column comprises at least 30 trays.

Embodiment 8 is an embodiment of embodiments 1-7, wherein the first column comprises a condenser and wherein the condenser uses chilled water.

Embodiment 9 is an embodiment of embodiments 1-8, wherein the acetonitrile product stream comprises less than 1 wt. % methanol, wherein the feedstock stream further comprises oxazole and propionitrile, wherein the acetonitrile stream comprises less than 0.01 wt. % hydrogen cyanide, and wherein the acetonitrile product stream comprises greater than 99.5 wt. % acetonitrile.

Embodiment 10 is an embodiments of embodiments 1-9, wherein the purifying comprises: treating the first intermediate acetonitrile stream comprising acetonitrile, oxazole, and hydrogen cyanide to produce a second intermediate acetonitrile stream comprising less than 1 wt % acrylonitrile and less than 1 wt % hydrogen cyanide.

Embodiment 11 is an embodiments of embodiments 1-10, wherein the purifying comprises: distilling the second intermediate acetonitrile stream to produce: a third distillate comprising acetonitrile, less than 50 wt % water and greater than 0.1 wt % oxazole; and a third bottoms comprising greater than 90 wt % acetonitrile and allyl alcohol.

Embodiment 12 is an embodiments of embodiments 1-11, wherein the purifying comprises: distilling the third bottoms to produce: a fourth distillate comprising greater than 95 wt % acetonitrile; and a fourth bottoms comprising greater than 1 wt % allyl alcohol and greater than 5 wt % propionitrile.

Embodiment 13 is an embodiments of embodiments 1-12, wherein the purifying comprises: treating the fourth distillate in a resin bed to remove oxazole.

Embodiment 14 is an embodiments of embodiments 1-13, wherein the feedstock stream comprises greater than 0.05 wt. % methanol.

Embodiment 15 is an embodiments of embodiments 1-14, wherein the feedstock stream comprises less than 25 wt. % acetonitrile.

Embodiment 16 is an embodiments of embodiments 1-15, wherein the feedstock stream further comprises propionitrile.

Embodiment 17 is an embodiments of embodiments 1-16, wherein the acetonitrile stream comprises less than 0.05 wt. % hydrogen cyanide.

While the invention has been described in detail, modifications within the spirit and scope of the invention will be readily apparent to those of skill in the art. In view of the foregoing discussion, relevant knowledge in the art and references discussed above in connection with the Background and Detailed Description, the disclosures of which are all incorporated herein by reference. In addition, it should be understood that aspects of the invention and portions of various embodiments and various features recited below and/or in the appended claims may be combined or interchanged either in whole or in part. In the foregoing descriptions of the various embodiments, those embodiments which refer to another embodiment may be appropriately combined with other embodiments as will be appreciated by one of skill in the art. Furthermore, those of ordinary skill in the art will appreciate that the foregoing description is by way of example only, and is not intended to limit.

We claim:

1. A process for producing acetonitrile, the process comprising:
    treating a feedstock stream comprising methanol, allyl alcohol, oxazole, acetonitrile, water, and hydrogen cyanide with a caustic solution to remove hydrogen cyanide and produce an acetonitrile stream comprising less than 1 wt. % hydrogen cyanide,
    distilling the acetonitrile stream in a first distillation column operated at a pressure ranging from 100 kPa to 175 kPa to produce:
    a first distillate comprising oxazole and methanol;
    a first intermediate acetonitrile stream comprising acetonitrile and oxazole and less than 1 wt % allyl alcohol;
    a first bottoms stream comprising allyl alcohol, and water; and
    purifying the first intermediate acetonitrile stream to produce an acetonitrile product stream and a recycle stream comprising allyl alcohol.

2. The process of claim 1, wherein the first intermediate acetonitrile stream is a sidedraw, optionally taken in the upper 70% of the first distillation column.

3. The process of claim 1, wherein:
    the first distillate comprises greater than 1 wt % oxazole and greater than 5 wt % methanol;
    the first intermediate acetonitrile stream comprises greater than 25 wt % acetonitrile, less than 5 wt % oxazole, and less than 50 wt % water;
    the first bottoms stream comprises greater than 0.01 wt % allyl alcohol and greater than 75 wt % water.

4. The process of claim 1, wherein the recycle stream comprise a smaller amount of allyl alcohol than the first bottoms stream.

5. The process of claim 1, wherein the acetonitrile product stream comprising greater than 98 wt % acetonitrile.

6. The process of claim 1, wherein the first column comprises at least 30 trays.

7. The process of claim 1, wherein the first column comprises a condenser and wherein the condenser uses chilled water.

8. The process of claim 1, wherein the acetonitrile product stream comprises less than 1 wt. % methanol, wherein the feedstock stream further comprises oxazole and propionitrile, wherein the acetonitrile stream comprises less than 0.01 wt. % hydrogen cyanide, and wherein the acetonitrile product stream comprises greater than 99.5 wt. % acetonitrile.

9. The process of claim 1, wherein the purifying comprises:
    treating the first intermediate acetonitrile stream comprising acetonitrile, oxazole, and hydrogen cyanide to produce a second intermediate acetonitrile stream comprising less than 1 wt % acrylonitrile and less than 1 wt % hydrogen cyanide.

10. The process of claim 9, wherein the purifying comprises:
    distilling the second intermediate acetonitrile stream to produce a third distillate comprising acetonitrile, less than 50 wt % water and greater than 0.1 wt % oxazole; and
    a third bottoms comprising greater than 90 wt % acetonitrile and allyl alcohol.

11. The process of claim 10, wherein the purifying comprises:
    distilling the third bottoms to produce:
    a fourth distillate comprising greater than 95 wt % acetonitrile; and
    a fourth bottoms comprising greater than 1 wt % allyl alcohol and greater than 5 wt % propionitrile.

12. The process of claim 11, wherein the purifying comprises:
    treating the fourth distillate in a resin bed to remove oxazole.

13. The process of claim 1, wherein the feedstock stream comprises greater than 0.05 wt. % methanol, less than 25 wt. % acetonitrile, and propionitrile.

14. The process of claim 1, wherein the acetonitrile stream comprises less than 0.05 wt. % hydrogen cyanide.

15. A process for producing acetonitrile, the process comprising:
    treating a feedstock stream comprising methanol, allyl alcohol, oxazole, acetonitrile, water, and hydrogen cyanide with a caustic solution to remove hydrogen cyanide and produce an acetonitrile stream comprising less than 1 wt. % hydrogen cyanide,
    distilling the acetonitrile stream in a first distillation column operated at a pressure ranging from 100 kPa to 175 kPa to produce to yield at least a first intermediate acetonitrile stream comprising acetonitrile and oxazole and less than 1 wt % allyl alcohol;
    treating the first intermediate acetonitrile stream to produce a second intermediate acetonitrile stream comprising less than 1 wt % acrylonitrile and less than 1 wt % hydrogen cyanide; and
    distilling the second intermediate acetonitrile stream to produce:
    a third distillate comprising acetonitrile, less than 50 wt % water and greater than 0.1 wt % oxazole; and
    a third bottoms comprising greater than 90 wt % acetonitrile and allyl alcohol.

16. The process of claim 15, wherein the first intermediate acetonitrile stream is a sidedraw, optionally taken in the upper 70% of the first distillation column.

17. The process of claim 15, wherein the third bottoms comprises greater than 98 wt % acetonitrile.

18. The process of claim 15, further comprising distilling the third bottoms to produce:
    a fourth distillate comprising greater than 95 wt % acetonitrile; and
    a fourth bottoms comprising greater than 1 wt % allyl alcohol and greater than 5 wt % propionitrile.

19. The process of claim 18, wherein the fourth distillate comprises greater than 98 wt % acetonitrile.

20. The process of claim 1, wherein the caustic solution comprises sodium hydroxide, potassium hydroxide, magnesium hydroxide; calcium hydroxide, or combinations thereof.

* * * * *